US012678403B2

(12) United States Patent
Jang

(10) Patent No.: US 12,678,403 B2
(45) Date of Patent: Jul. 14, 2026

(54) PHARMACEUTICAL COMPOSITION FOR PREVENTING OR TREATING OBESITY OR NON-ALCOHOLIC FATTY LIVER CONTAINING POLYGALIN C AS ACTIVE INGREDIENT

(71) Applicant: UNIVERSITY-INDUSTRY COOPERATION GROUP OF KYUNG HEE UNIVERSITY, Yongin-si (KR)

(72) Inventor: Hyeung Jin Jang, Seoul (KR)

(73) Assignee: UNIVERSITY-INDUSTRY COOPERATION GROUP OF KYUNG HEE UNIVERSITY, Yongin-si (KR)

( * ) Notice: Subject to any disclaimer, the term of this patent is extended or adjusted under 35 U.S.C. 154(b) by 417 days.

(21) Appl. No.: 18/287,015

(22) PCT Filed: Apr. 8, 2022

(86) PCT No.: PCT/KR2022/005097
§ 371 (c)(1),
(2) Date: Oct. 15, 2023

(87) PCT Pub. No.: WO2022/220497
PCT Pub. Date: Oct. 20, 2022

(65) Prior Publication Data
US 2024/0189226 A1 Jun. 13, 2024

(30) Foreign Application Priority Data

Apr. 16, 2021 (KR) ........................ 10-2021-0049683
Apr. 6, 2022 (KR) ........................ 10-2022-0042610

(51) Int. Cl.
*A61K 9/00* (2006.01)
*A61K 31/7048* (2006.01)
*A61P 3/06* (2006.01)

(52) U.S. Cl.
CPC ........ *A61K 9/0056* (2013.01); *A61K 31/7048* (2013.01); *A61P 3/06* (2018.01)

(58) Field of Classification Search
CPC ............................ A61K 31/7048; A61K 36/69
See application file for complete search history.

(56) References Cited

U.S. PATENT DOCUMENTS

2024/0115645 A1* 4/2024 Zhang .................. A61K 31/352

FOREIGN PATENT DOCUMENTS

| JP | 2009-046465 A | 3/2009 |
| KR | 10-2004-0060808 A | 7/2004 |
| KR | 10-2014-0140674 A | 12/2014 |
| KR | 10-2014-0147668 A | 12/2014 |

OTHER PUBLICATIONS

Kou et al., Fitoterapia, 2006, 77, p. 411-415. (Year: 2006).*
Li et al., Journal of Asian Natural Products Research, 2006, 8(5), p. 401-409. (Year: 2006).*
International Search Report for PCT/KR2022/005097 mailed Jul. 21, 2022 from Korean Intellectual Property Office.
Wang, Chun-Chung et al., "Polygala tenuifolia extract inhibits lipid accumulation in 3T3-LI adipocytes and high-fat diet-induced obese mouse model and affects hepatic transcriptome and gut microbiota profiles", Food & Nutrition Research, 2017, vol. 61, article No. 1379861, inner pp. 1-17.
Lee, Ji-Hye et al., The Herbal Medicine KBH-1 Inhibits Fat Accumulation in 3T3-LI Adipocytes and Reduces High Fat Diet-Induced Obesity through Regulation of the AMPK Pathway, PLoS ONE, Dec. 9, 2015 (publication date), vol. 10, article No. e0142041, inner pp. 1-18.

* cited by examiner

*Primary Examiner* — Jonathan S Lau
(74) *Attorney, Agent, or Firm* — Revolution IP, PLLC

(57) ABSTRACT

The present invention relates to a pharmaceutical composition for preventing or treating obesity, wherein the pharmaceutical composition contains Polygalin C as an active ingredient. The Polygalin C not only reduces the accumulation of lipids by inhibiting the differentiation of preadipocytes into adipocytes, but also inhibits adipose tissue generation factors and adipogenic factors and modulates AMPK/ACC and MAPK/Akt signaling pathways to inhibit the differentiation of adipocytes, and thus can treat obesity more effectively. In addition, the present invention inhibits adipogenic factors and inflammatory factors in a free fatty acid-induced non-alcoholic steatohepatitis (NASH) cell model, and thus can effectively treat and prevent non-alcoholic fatty liver disease (NAFLD) including hepatic steatosis and non-alcoholic steatohepatitis.

6 Claims, 6 Drawing Sheets

Specification includes a Sequence Listing.

[FIG. 1]
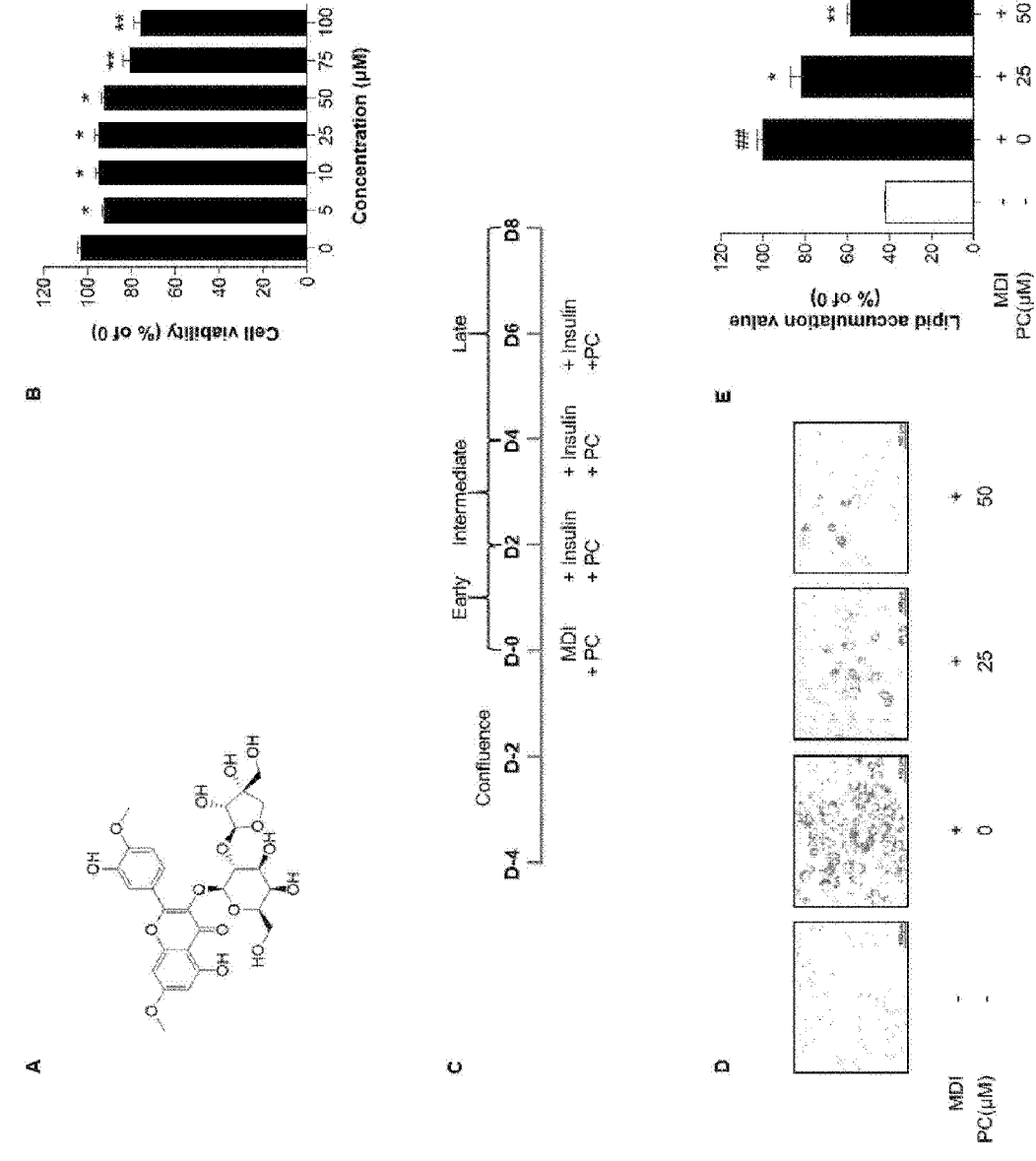

[FIG. 2]
A
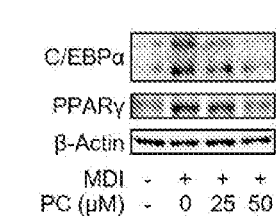
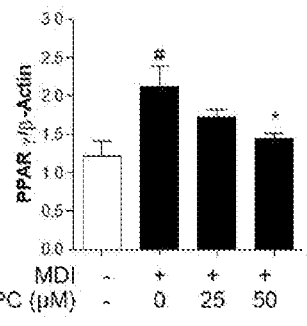
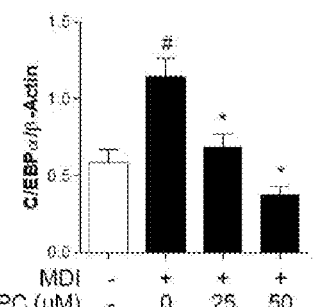
B
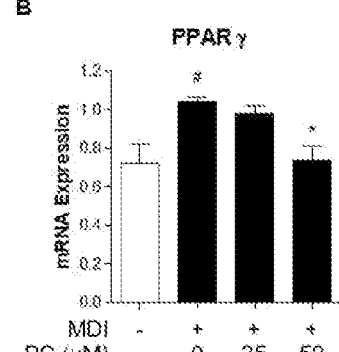
C
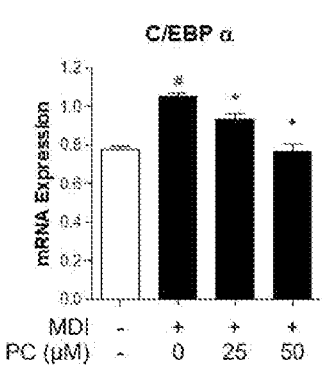
D
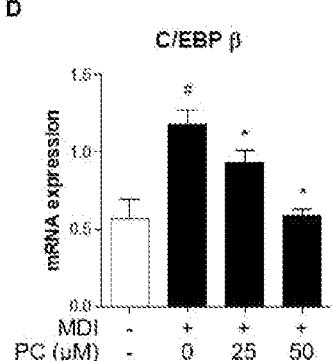
E
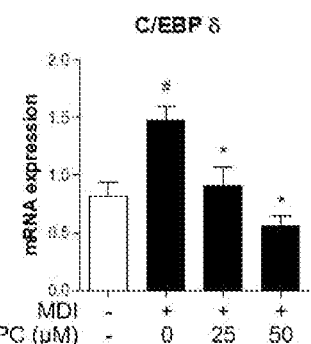

[FIG. 3]
A
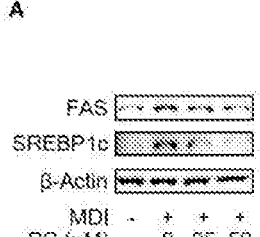
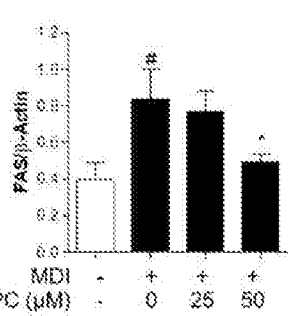
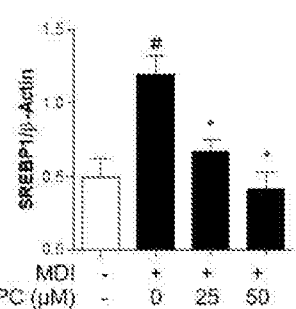
B　FAS　　　　　　　C　SREBP1c
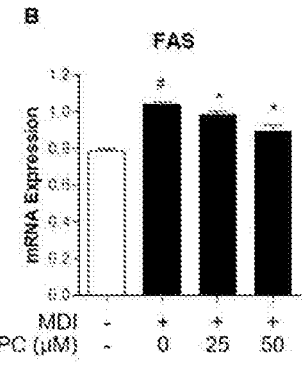
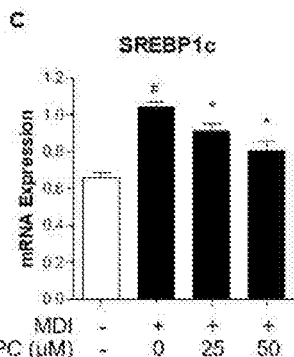
D
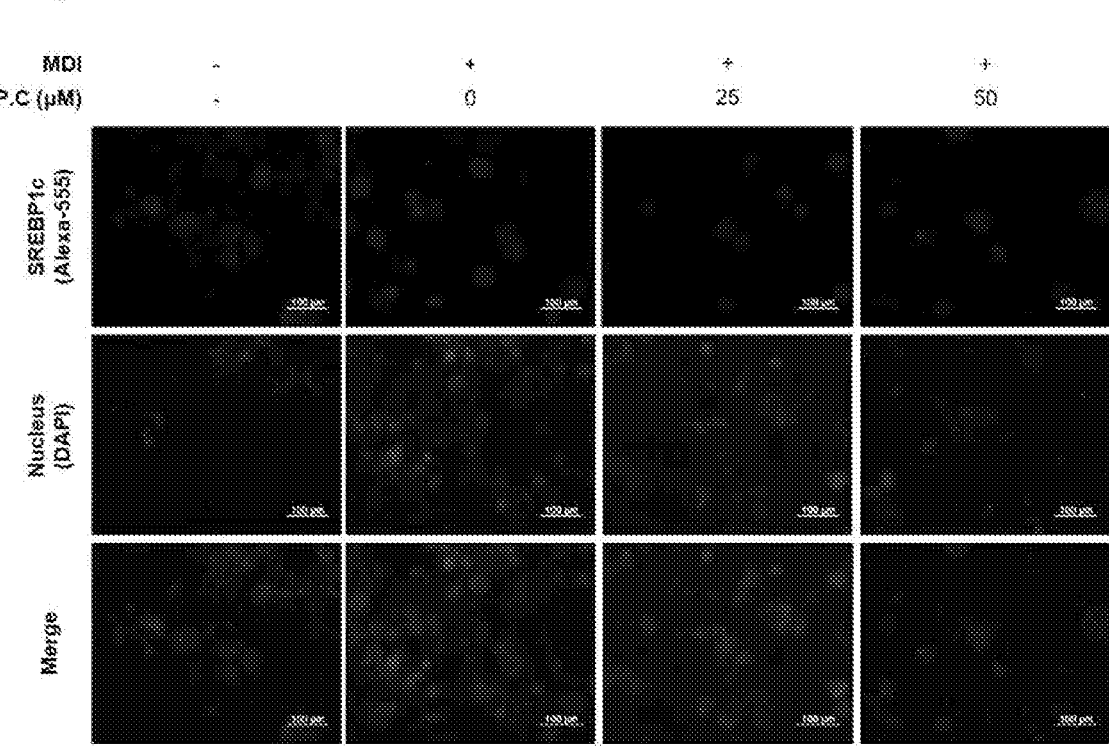

[FIG. 4]
A
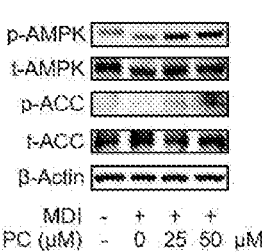 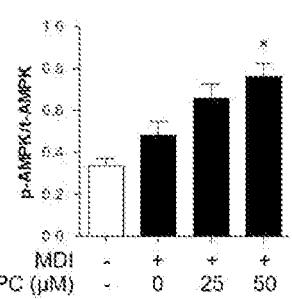 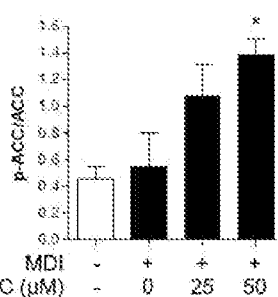
B
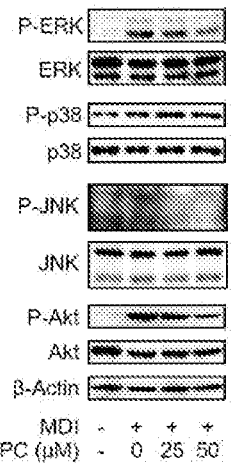 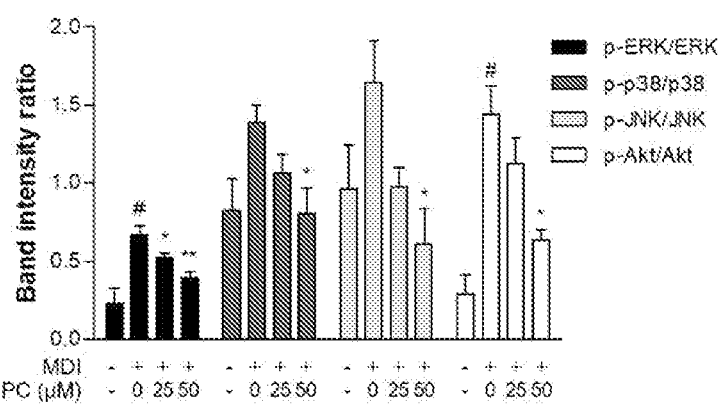

[FIG. 5]
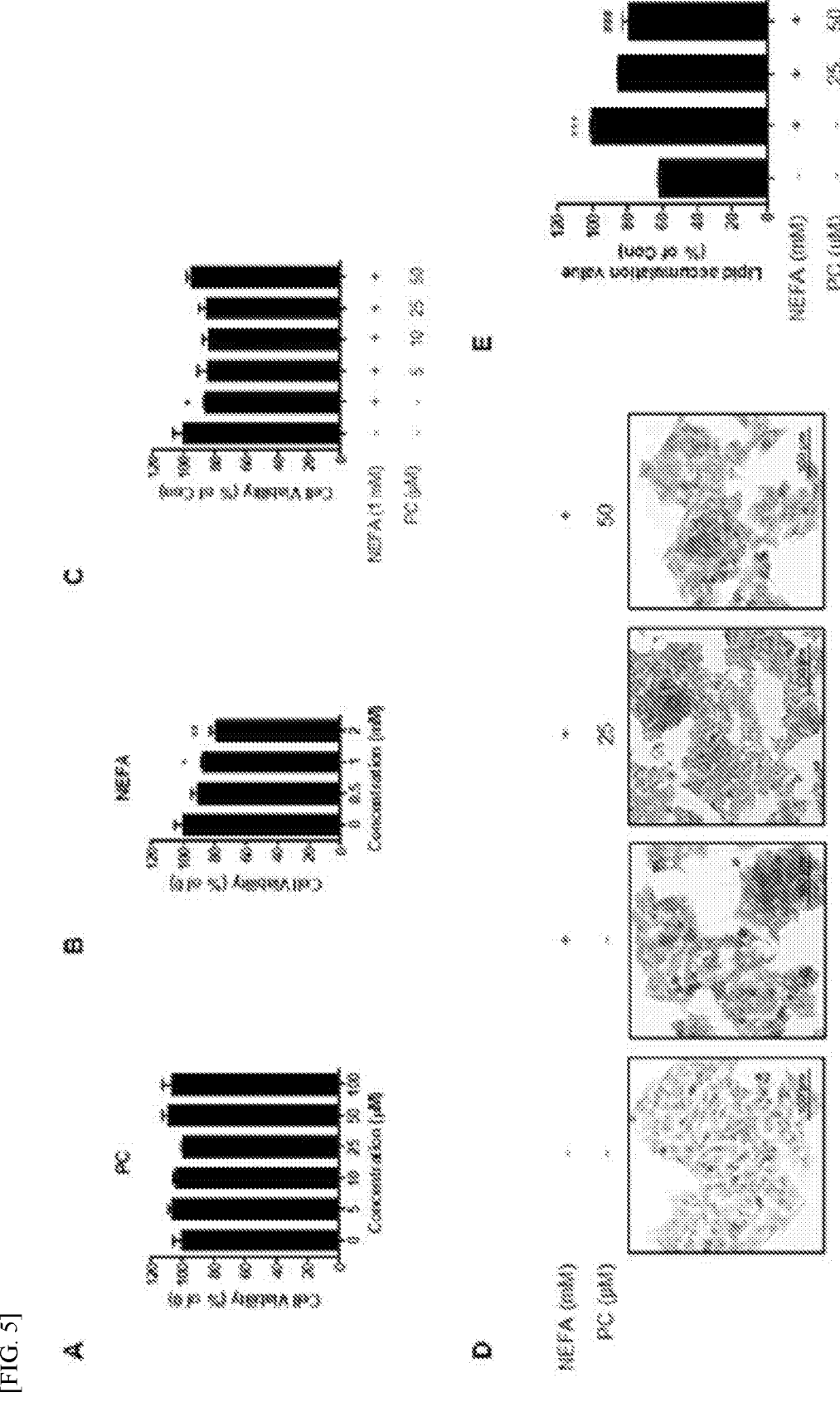

[FIG. 6]
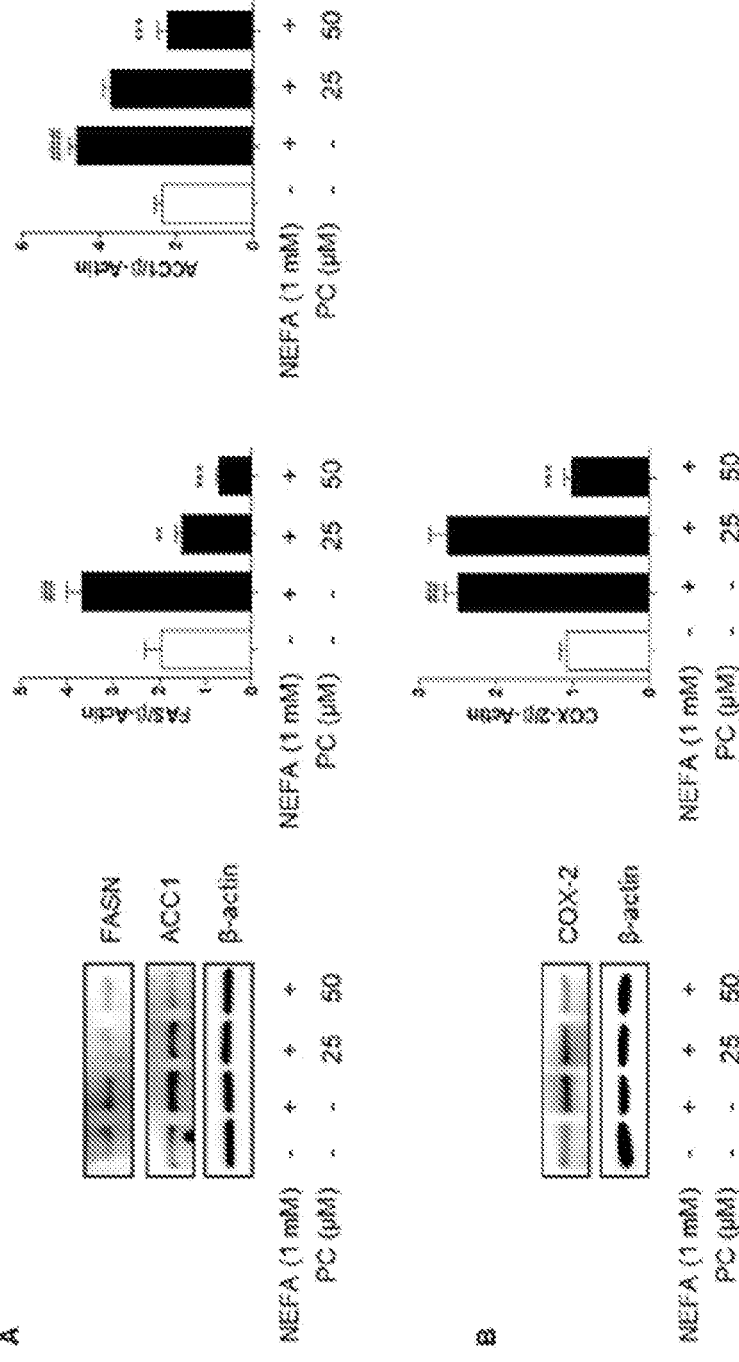

PHARMACEUTICAL COMPOSITION FOR PREVENTING OR TREATING OBESITY OR NON-ALCOHOLIC FATTY LIVER CONTAINING POLYGALIN C AS ACTIVE INGREDIENT

CROSS REFERENCE TO PRIOR APPLICATIONS

This application is a National Stage Application of PCT International Patent Application No. PCT/KR2022/005097 filed on Apr. 8, 2022, under 35 U.S.C. § 371, which claims priority to Korean Patent Application Nos. 10-2021-0049683 filed Apr. 16, 2021 and 10-2022-0042610 filed Apr. 6, 2022, respectively, which are all hereby incorporated by reference in their entirety.

SEQUENCE LISTING

This application contains a Sequence Listing submitted via EFS-Web and hereby incorporated by reference in its entirety. The Sequence Listing is named SEQCRF_2280-474.txt, created on Jan. 28, 2024, and 3,287 bytes in size.

TECHNICAL FIELD

The present disclosure provides a pharmaceutical composition for preventing or treating obesity or non-alcoholic fatty liver, including Polygalin C as an active ingredient.

BACKGROUND ART

Obesity, which is characterized by an increase in the number and size of adipocytes due to an imbalance between food intake and energy consumption, is a major cause of chronic diseases such as type 2 diabetes, hypertension, arteriosclerosis, arthritis, hyperlipidemia, simple hepatic steatosis, and non-alcoholic steatohepatitis (NASH).

Various synthetic drugs that are approved by the U.S. Food and Drug Administration (FDA) exist to treat obesity in addition to therapies for obesity, but they have side effects in the body in the long-term use. Therefore, many researchers have studied the anti-obesity effect of natural products showing excellent stability, discovering that differentiation from preadipocytes to adipocytes in the development of obesity is an important process that causes hypertrophy and proliferation of adipose tissues. Thus, inhibiting differentiation of preadipocytes into adipocytes is a potential strategy for preventing obesity.

In general, 3T3-L1 adipocytes derived from mouse embryos are primarily used to investigate mechanisms related to obesity. Differentiation of adipocytes requires inducing factors (MDIs), including 3-isobutyl-1-methylxanthine (IBMX), dexamethasone, and insulin. CCAAT/enhancer-binding proteins (C/EBPs) having six types are also involved in the process of adipogenesis, all of which C/EBPα, β, γ, and δ are associated with adipose tissue generation. During MDI-induced differentiation, C/EBPβ and C/EBPδ activate initiation of the adipogenesis process to upregulate C/EBPα and peroxisome proliferator-activated receptor γ (PPARγ). Acetyl-CoA and fatty acid synthase (FAS) are involved in adipogenesis, including fatty acid synthesis and lipid accumulation. Although AMP-activated protein kinase (AMPK) is a major factor in regulating energy balance in cells, the protein also plays a role in adipose tissue generation by regulating sterol regulatory element-binding protein 1c (SREBP1c), which is involved in the process of adipose tissue generation and adipogenesis. Phosphoinositide 3-kinase/protein kinase B (Akt) and mitogen-activated protein kinase (MAPK) signaling pathways have an overall impact on the differentiation process and induce expression of adipose tissue generation factors.

Therefore, it is still necessary to develop a safe therapeutic agent for obesity that is capable of inhibiting differentiation of preadipocytes into adipocytes, with less toxicity.

On the other hand, non-alcoholic fatty liver disease (NAFLD) refers to a disease in which triglycerides are accumulated in the liver regardless of alcohol consumption, including steatosis and non-alcoholic steatohepatitis (NASH). Non-alcoholic steatohepatitis was first named by Ludwig et al. in 1980 and is characterized by inflammation or fibrosis along with fatty liver. Fatty liver is considered to be a benign disease with a favorable clinical prognosis, but non-alcoholic steatohepatitis is a progressive liver disease that is recognized as a prodromal condition that causes hepatocirrhosis or liver cancer. It is called a silent disease since there are no symptoms that a patient may feel during progression to non-alcoholic steatohepatitis. On the other hand, it is known that 20 to 30% of fatty liver patients undergo steatohepatitis with inflammation and fibrosis accompanied, such that the importance of treatment in the fatty liver stage with a good clinical prognosis is increasing.

As a result of analyzing the prevalence of liver disease in 14,438 people participated in 1998~2001 and 11,455 people in 2016~2017 in the recent National Health Survey, the prevalence of non-alcoholic fatty liver is high in Korea, with an increase by 16% from 18.6% to 21.5%. In addition, since NASH is a disease for which there is no approved therapeutic agent worldwide so far with high burden on patients and which eventually leads to a liver transplant, according to the US Drug Administration (FDA), there is a high demand for therapeutic agents that may slow the progression of non-alcoholic fatty liver and non-alcoholic steatohepatitis or alleviate symptoms. The main pathogenesis mechanisms of non-alcoholic fatty liver include 1) excessive fat accumulation in hepatocytes due to imbalance in fatty acid metabolism, 2) inflammatory reactions such as TNFα and IL1β due to accumulated lipotoxicity in hepatocytes, and 3) an increase in oxidative stress. To date, in an attempt to treat non-alcoholic fatty liver including non-alcoholic steatohepatitis, many researchers have developed drugs regulating secretion of inflammatory cytokine TNF or targeting an inhibitor of a CCR2 receptor on monocytes, regulation of a CD163 receptor in kupffer cells, an FXR receptor inhibitor, and an agonist of PPARγ or PPARδ/α, but no drug has yet been approved as a definitive therapeutic agent, largely due to limitations of synthetic compound drugs regarding toxicity-related side effects.

Therefore, there is still a need for additional development of therapeutic agents using natural or biological substances that are thought to be relatively less toxic.

DISCLOSURE OF THE INVENTION

Technical Goals

An object of the present disclosure is to provide a pharmaceutical composition for preventing or treating obesity, including Polygalin C as an active ingredient.

Another object of the present disclosure is to provide a health functional food composition for reducing body fat, including Polygalin C as an active ingredient.

Another object of the present disclosure is to provide a pharmaceutical composition for preventing or treating non-alcoholic fatty liver, including Polygalin C as an active ingredient.

Another object of the present disclosure is to provide a health functional food composition for preventing or ameliorating non-alcoholic fatty liver, including Polygalin C as an active ingredient.

Technical Solutions

In order to achieve the above object, the present disclosure provides a pharmaceutical composition for preventing or treating obesity, including Polygalin C as an active ingredient.

In addition, the present disclosure provides a health functional food composition for reducing body fat, including Polygalin C as an active ingredient.

In addition, the present disclosure provides a pharmaceutical composition for preventing or treating non-alcoholic fatty liver, including Polygalin C as an active ingredient.

In addition, the present disclosure provides a health functional food composition for preventing or ameliorating non-alcoholic fatty liver, including Polygalin C as an active ingredient.

Advantageous Effects

The present disclosure relates to a composition for preventing or treating obesity or non-alcoholic fatty liver including Polygalin C as an active ingredient, wherein Polygalin C not only inhibits differentiation of preadipocytes, but also inhibits adipose tissue generation factors and adipogenic factors and thus is a safe material that is excellent in an obesity treatment effect and effective in the treatment of non-alcoholic fatty liver by inhibiting inflammatory factors, such that Polygalin C is very effective in treatment of obesity or non-alcoholic fatty liver and applicable in various forms such as drugs for treatment of obesity or non-alcoholic fatty liver or health functional foods for reducing body fat.

BRIEF DESCRIPTION OF DRAWINGS

FIG. 1 shows experimental results illustrating inhibition of lipid accumulation by Polygalin C (hereinafter referred to as PC) in 3T3-L1 adipocytes.

FIG. 2 shows experimental results illustrating PC inhibition at an expression level of transcription factors related to adipose tissue generation in 3T3-L1 adipocytes.

FIG. 3 shows experimental results of effects of PC on an expression level of adipogenic factors in 3T3-L1 adipocytes.

FIG. 4 shows experimental results of effects of PC on expression of AMPK/ACC and MAPK/Akt signaling pathways in 3T3-L1 adipocytes.

FIG. 5 shows experimental results illustrating effects of PC in a fatty liver model induced by treatment of 1 mM non esterified fatty acid (hereinafter referred to as NEFA) in HepG2 hepatocytes.

FIG. 6 shows experimental results illustrating effects of PC on expression of adipogenic factors and inflammatory factors in fatty liver-induced HepG2 cells.

BEST MODE FOR CARRYING OUT THE INVENTION

Hereinafter, the present disclosure will be described in detail.

Existing therapeutic agents for obesity frequently cause side effects in the body in the long-term use, so the inventors have put effort into research to discover a material that is safer and has an excellent obesity treatment effect, thereby completing the present disclosure by discovering that Polygalin C inhibits differentiation of preadipocytes into adipocytes and inhibits adipose tissue generation factors and adipogenic factors.

The present disclosure provides a pharmaceutical composition for preventing or treating obesity, including Polygalin C as an active ingredient.

The obesity may be selected from obesity caused by a high-fat diet or obesity caused by hormonal deficiency due to menopause, but is not limited thereto.

The Polygalin C may inhibit differentiation of preadipocytes into adipocytes to suppress accumulation of lipids.

The Polygalin C may inhibit adipose tissue generation transcription factors and adipogenic factors.

The adipose tissue generation transcription factor may be one or more selected from the group consisting of a peroxisome proliferator-activated receptor γ (PPARγ) and CCAAT/enhancer-binding protein (C/EBP), but is not limited thereto.

The adipogenic factor may be one or more selected from the group consisting of sterol regulatory element-binding protein 1 (SREBP1) and fatty acid synthase (FAS), but is not limited thereto.

The Polygalin C may regulate signaling pathways of one or more selected from the group consisting of AMP-activated protein kinase/acetyl-CoA (AMPK/ACC) and mitogen-activated protein kinase/protein kinase B (MAPK/Akt), but is not limited thereto. As an example embodiment, AMPK/ACC is activated by treatment of the Polygalin C in MDI-treated adipocytes, and MAPK/Akt is inhibited to suppress adipocyte differentiation.

The Polygalin C may be contained in an amount of 0.01 to 50 parts by weight with respect to a total of 100 parts by weight of the pharmaceutical composition.

The Polygalin C may be separated or extracted by a method well known in the art, prepared by a chemical synthesis method, and selected on the market to be used, but the method or substance is not particularly limited.

In another example embodiment of the present disclosure, the pharmaceutical composition may further include one or more appropriate additives selected from the group consisting of carriers, excipients, disintegrants, sweeteners, coating agents, swelling agents, antifrictions, lubricants, flavoring agents, antioxidants, buffers, bacteriostatic agents, diluents, dispersants, surfactants, binders, and lubricants that are commonly used in the preparation of pharmaceutical compositions. Specifically, lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate, and mineral oil may be used as carriers, excipients, and diluents, and solid preparations for oral administration include tablets, pills, powder, granules and capsules, wherein such solid preparation may be prepared by mixing, in the composition, at least one or more excipients such as starch, calcium carbonate, sucrose or lactose, and gelatin. In addition to simple excipients, lubricants such as magnesium stearate and talc may also be used. Liquid preparations for oral use include suspensions, solutions, emulsions, and syrups, and various excipients such as wetting agents, sweeteners, fragrances, and preservatives may be included in addition to commonly used simple diluents such as water and liquid paraffin. Formulations for parenteral administration include sterile aqueous solutions, non-aqueous solutions, suspensions, emulsions, freeze-dried preparations, and suppositories. Propylene glycol, polyethylene glycol, vegetable oils such as olive oil, and injectable esters such as ethyl oleate may be used as non-aqueous solvents and suspensions. Witepsol, macrogol, Tween 61, cacao butter, laurin fat, and glycerogelatin may be used as a base of the suppositories. According to an example embodiment of the present disclosure, the pharmaceutical composition may be administered to a subject in a conventional manner via intravenous, intraarterial, intraperitoneal, intramuscular, intraarterial, intraperitoneal, intrasternal, transdermal, intranasal, inhalational, topical, rectal, oral, intraocular, or intradermal routes. The dosage of the active ingredient according to the present disclosure may vary depending on the condition and weight of a subject, the type and severity of diseases, the drug form, the route of administration and duration and be appropriately selected by those skilled in the art, and the daily dosage may be 0.01 mg/kg to 200 mg/kg, preferably 0.1 mg/kg to 200 mg/kg, more preferably 0.1 mg/kg to 100 mg/kg. Administration may be conducted once a day or in several divided doses, thereby not limiting the scope of the present disclosure.

In addition, the present disclosure provides a health functional food composition for reducing body fat, including Polygalin C as an active ingredient.

The health functional food may include various nutritional supplements, vitamins, minerals (electrolytes), flavoring agents such as synthetic flavors and natural flavors, colorants and thickening agents (cheese, chocolate), pectic acid and salts thereof, alginic acid and salts thereof, organic acids, protective colloidal thickeners, pH regulators, stabilizers, preservatives, glycerin, alcohol, and carbonating agents used in carbonated beverages. It may also include pulp for the manufacture of natural fruit juices, synthetic fruit juices, and vegetable beverages. These components may be used independently or in combination. In addition, the health functional food composition may be in any one form of meat, sausage, bread, chocolate, candy, snacks, confectionery, pizza, ramen, chewing gum, ice cream, soup, beverage, tea, functional water, drink, alcohol, and vitamin complex. In addition, the health functional food may further include food additives, and the suitability as the "food additive" is determined by the standards and criteria related to corresponding items according to the general rules and general test methods of Korean Food Additives Codex approved by the Ministry of Food and Drug Safety, unless otherwise stipulated. The items listed in the "Korean Food Additives Codex" may include, for example, chemically synthesized compounds such as ketones, glycine, potassium citrate, nicotinic acid, and cinnamic acid, natural additives such as persimmon color, licorice extracts, crystallized cellulose, kaoliang color, and guar gum, and mixed preparations such as sodium L-glutamate preparations, noodle-added alkali agents, preservative agents, and tar color agents. In this case, the content of the active ingredient added to the food in the process of manufacturing the health functional food may be appropriately adjusted as needed.

In addition, the present disclosure provides a pharmaceutical composition for non-alcoholic fatty liver, including Polygalin C as an active ingredient.

The non-alcoholic fatty liver may be selected from hepatic steatosis or non-alcoholic steatohepatitis, but is not limited thereto.

In addition, the present disclosure provides a health functional food composition for preventing or ameliorating non-alcoholic fatty liver, including Polygalin C as an active ingredient.

MODES FOR CARRYING OUT THE INVENTION

Hereinafter, example embodiments will be described in detail to help the understanding of the present disclosure. However, the following example embodiments are merely illustrative of the content of the present disclosure, and the scope of the present disclosure is not limited to the following example embodiments. The example embodiments of the present disclosure are provided to more completely explain the present disclosure to those of ordinary skill in the art.

Preparation Example 1

Chemicals

Polygalin C (hereinafter referred to as PC) was obtained from Chemfaces (Wuhan Chemfaces Biochemical Co., Ltd., Wuhan, China).

Preparation Example 2

Reagents

Dulbecco's modified Eagle's medium (DMEM) and fetal bovine serum (FBS) were purchased from Gibco (Grand Island, NY, USA). Phosphate buffered saline (PBS) and Roswell Park Memorial Institute 1640 (RPMI-1640) were purchased from Corning (NY, USA). IBMX, dexamethasone, insulin, oleic acid, palmitic acid, and Oil Red O powder were obtained from Sigma-Aldrich (St. Louis, MO, USA). 3-(4,5-dimethylthiazol-2-yl)-2,5-diphenyltetrazolium bromide (MTT) was purchased from Invitrogen (Carlsbad, CA, USA). The enhanced chemiluminescence solutions (WestGlow Pico PLUS solA and solB) were purchased from Biomax Co., Ltd. (Seoul, Korea). The reagent for Bradford protein assay was purchased from Bio-Rad (Hercules, CA, USA). COX-2, PPARγ, FAS, phospho-acetyl-CoA carboxylase (p-ACC), total ACC (t-ACC), phospho-AMPK (p-AMPK), total AMPK (t-AMPK), phospho-extracellular signal-regulated kinase (p-ERK), total ERK (t-ERK), phospho-c-Jun N-terminal kinase (p-JNK), total JNK (t-JNK), phospho-Akt (p-Akt), total Akt (t-Akt), phospho-p38 (p-p38), and total p38 (t-p38) antibodies were purchased from Cell Signaling Technology (Danvers, MA, USA). C/EBPα, SREBP1c, β-actin, and anti-rabbit and anti-mouse secondary antibodies were purchased from Santa Cruz Biotechnology (Dallas, TX, USA).

Experimental Example 1

Cell Culture

The mouse embryonic fibroblast line 3T3-L1 cells and the human liver cell line HepG2 were obtained from the American Type Culture Collection (Rockville, MD, USA). DMEM medium was used for 3T3-L1 cells and RPMI medium for HepG2 cells, and each medium was supplemented with 10%

FBS and 100 U/mL penicillin. Both cells were cultured in a cell incubator at 37° C. in the presence of 5% $CO_2$.

3T3-L1 cells were inoculated into a 6-well plate in a density of $8\times10^4$ cells/well, and the medium was replaced until the confluence is satisfied. For differentiation, cells were incubated in differentiation media (0.5 mM IBMX, 0.5 µM dexamethasone, and 1 µg/mL insulin). The medium was then replaced with a maintenance culture including 1 µg/mL insulin and PC (0-50 µM) once every 2 days. An outline of the experimental process is shown in FIG. 1C.

HepG2 cells were inoculated into a 6-well plate in a density of $3\times10^5$ cells/well and incubated for one day. Then, for fatty liver induction, an FBS-free RPMI medium supplemented with 1% bovine serum albumin (BSA) and NEFA (0.66 mM oleic acid and 0.33 mM palmitic acid) was treated, followed by incubation for 24 hours. When treated with PC (0-50 µM), fatty liver induction medium was treated together for incubation for 24 hours.

Experimental Example 2

MTT Assay

3T3-L1 preadipocytes were inoculated into a 96-well cell culture plate by $1\times10^4$ cells/well and incubated overnight. The medium was then replaced with DMEM including different concentrations of PC (0, 5, 10, 25, 50, 75, and 100 µM) for 48 hours.

HepG2 hepatocytes were inoculated into a 96-well cell culture plate by $1\times10^4$ cells/well and incubated overnight. Then, for 24 hours, they were replaced with fatty liver induction media including different concentrations of PC (0, 5, 10, 25, 50, and 100 µM).

After PC treatment, cells were incubated with MTT solution (0.5 mg/ml dissolved in PBS) for 2 hours. After incubation, the medium in each well was removed, and dimethyl sulfoxide was added to dissolve the precipitated formazan. When formazan was completely dissolved, the absorbance was measured at 540 nm using a microplate reader (Bio-Rad) to determine cell viability.

Experimental Example 3

Immunoblotting

Cell lysis buffer (Cell Signaling Technology) was used to lyse cells. The reagent for Bio-Rad protein assay was used to measure protein concentrations for Bradford assay. Each sample was separated by sodium dodecyl sulfate polyacrylamide gel electrophoresis using 8% acrylamide gel and then electrotransferred to a nitrocellulose membrane. The membrane was blocked with 3% bovine serum albumin (BSA) in Tris buffered saline/Tween 20 (TBS-T) at 4° C. for 1 hour and incubated overnight at 4° C. with COX-2, C/EBPα, PPARγ, SREBP1c, FAS, p-ACC, t-ACC, p-AMPK, t-AMPK (1:2000), and β-actin (1:10,000) antibodies. The membrane was extensively washed with TBS-T at 3 or more times for 30 minutes and incubated with goat anti-rabbit IgG-horseradish peroxidase (HRP) and goat anti-mouse IgG-HRP (1:10,000 all in TBS-T) secondary antibodies for 1 hour.

Experimental Example 4

Oil Red O Analysis

The treated cells were washed with PBS and fixed with 10% formalin for 1 hour. The cells were then washed with 60% isopropanol and dried completely. A 60% Oil Red O working solution diluted in distilled water (DW) was added to the cells. In the case of hepatocytes, in order to observe the morphology of the cells, they were additionally treated with hematoxylin for 1 minute for staining. The stained cells were washed with DW 3 times and photographed using the Olympus IX71 microscope (Olympus, Tokyo, Japan). To quantify lipid accumulation, stained cells were dissolved in 100% isopropanol, and measurement was performed at 490 nm with a microplate reader (Bio-Rad).

Experimental Example 5

Immunofluorescence Analysis

The cells were treated with or without PC in a 4-well confocal dish. After treatment, the cells were fixed with 10% formalin for 10 minutes, treated with 0.2% Triton X diluted in PBS for 20 minutes, washed with PBS 3 times, and blocked with 5% BSA dissolved in PBS for 1 hour. Next, cells were incubated overnight in the presence of anti-SREBP1 antibodies (1:500 in PBS) at 4° C., followed by incubation in the presence of Alexa Fluor-555 antibody for 1 hour at room temperature. The cell nucleus was stained with 4,6-diamidino-2-phenylindole (DAPI: Sigma-Aldrich) at room temperature for 3 minutes. DAPI-stained cells were washed with PBS for 30 minutes, and fluorescence was observed using CELENA™ S Digital Imaging System (Logos Biosystems, Inc.).

Experimental Example 6

Total RNA Isolation and Real-Time Polymerase Chain Reaction (PCR)

Cells were treated with Ribo-Ex to extract RNA using GeneAll Hybrid-R RNA purification kit (GeneAll, Seoul, Korea). RNA was quantified using NanoDrop (Thermo Fisher Scientific). Amplification of complementary DNA was performed at 45° C. for 60 minutes and 95° C. for 15 minutes using a Maxime RT premix (iNtRON Biotechnology, South Korea). Real-time quantitative PCR was performed using the Universal SYBR Green Master Mix (Applied Biosystems, Foster City, CA, USA). Real-time PCR was performed on Applied Biosystems StepOne System (Applied Biosystems). In this study, relative target gene expression was quantified relatively to gene expression of glyceraldehyde 3-phosphate dehydrogenase to determine mRNA expression levels. The PCR primers used are shown in TABLE 1.

TABLE 1

| Gene | | Primer |
|------|---|--------|
| C/EBPβ | Forward | AGCGGCTGCAGAAGAAGGT (SEQ ID NO: 1) |
| | Reverse | GGCAGCTGCTTGAACAAGTTC (SEQ ID NO: 2) |
| C/EBPδ | Forward | TTCCAACCCCTTCCCTGAT (SEQ ID NO: 3) |
| | Reverse | CTGGAGGGTTTGTTTTTTCTGT (SEQ ID NO: 4) |
| PPARγ | Forward | GGTGAAACTCTGGGAGATTC (SEQ ID NO: 5) |
| | Reverse | CAACCATTGGGTCAGCTCTT (SEQ ID NO: 6) |

TABLE 1-continued

| Gene | | Primer |
|---|---|---|
| CEBP α | Forward | AGGTGCTGGAGTTGACCAGT (SEQ ID NO: 7) |
| | Reverse | CAGCCTAGAGATCCAGCGAC (SEQ ID NO: 8) |
| FAS | Forward | TTGCTGGCACTACAGAATGC (SEQ ID NO: 9) |
| | Reverse | AACAGCCTCCAGAGCGACAAT (SEQ ID NO: 10) |
| SREBP1c | Forward | ATCGCAAACAAGCTGACCTG (SEQ ID NO: 11) |
| | Reverse | AGATCCAGGTTTGAGGTGGG (SEQ ID NO: 12) |
| GAPDH | Forward | GCCACATCGCTCAGACACC (SEQ ID NO: 13) |
| | Reverse | CCCAATACGACCAAATCCGT (SEQ ID NO: 14) |

Experimental Example 7

Statistical Analysis

The data were represented by a mean±a standard error of mean of at least three different experiments. Statistical analysis was performed using one-way analysis of variance using GraphPad Prism 5 software (GraphPad Software, San Diego, CA, USA) followed by the Mann-Whitney test. The p-value <0.05 was considered statistically significant, while p<0.01 and p<0.001 were considered quite significant.

Example 1

Identification of Cytotoxicity of Polygalin C in 3T3-L1 Cells

In order to identify cytotoxicity of PC in 3T3-L1 cells, various concentrations of PC (0, 5, 10, 25, 50, 75, and 100 μM) were treated for 48 hours, and then cell viability was determined using MTT assay. As a result, according to FIG. 1B, PC showed a non-toxic effect to a concentration up to 50 μM.

Example 2

Identification of Effects of PC on Adipocyte Differentiation in 3T3-L1 Preadipocytes To investigate whether PC has an inhibitory effect on adipose tissue differentiation, cells were differentiated in the presence and absence of PC at various concentrations (0, 25, and 50 μM), and then Oil red O staining was used. As a result, according to FIGS. 1D and 1E, PC dose-dependently inhibited production of lipid droplets in 3T3-L1 cells compared to fully differentiated adipocytes. Thus, PC reduced accumulation of lipids in 3T3-L1 cells during adipose tissue generation differentiation.

Example 3

Identification of Effects of PC on Expression Levels of Adipose Tissue Generation Transcription Factors To investigate how PC inhibits adipose tissue generation in 3T3-L1 cells, investigation was performed on protein expression levels of key adipose tissue generation markers. C/EBPα and PPARγ are well-known major transcription factors in adipose tissue generation. Therefore, the expression of these factors was examined by Western blotting. As a result, according to FIG. 2A, the relative protein levels of C/EBPα and PPARγ were significantly increased in MDI-induced adipocytes, but that of the PC group was decreased dose-dependently compared to the MDI-induced group. Similarly, according to FIGS. 2B and 2C, mRNA expression levels of C/EBPα and PPARγ were also reduced compared to fully differentiated adipocytes.

In order to additionally identify expression of other adipose tissue generation markers such as C/EBPβ and C/EBPδ, mRNA levels of these markers were examined. As a result, according to FIGS. 2D and 2E, the corresponding value decreased concentration-dependently compared to adipocytes. Thus, these results showed that PC regulates adipose tissue generation by inhibiting C/EBPβ and C/EBPδ and inhibiting expression levels of adipose tissue generation transcription factors C/EBPα and PPARγ.

Example 4

Identification of Effects of PC on Expression Levels of Adipogenic Factors

In order to determine whether the PC inhibits the adipogenic factors, the degree of expression of the adipogenic factors was examined through Western blotting and real-time PCR. FAS and SREBP1 play an important role in adipogenesis, protein expression levels of which were investigated. As a result, according to FIG. 3A, PC significantly reduced the expression levels of FAS and SREBP1c dose-dependently compared to fully differentiated adipocytes. In addition, according to FIGS. 3B and 3C, the RNA level was reduced compared to fully differentiated adipocytes. In addition, according to FIG. 3D, a significant relieving effect of PC on the reduction of MDI-induced SREBP1c expression in adipocytes was observed through immunofluorescence analysis. These results showed that PC regulates adipose tissue generation by inhibiting FAS and SREBP1 activation in fully differentiated adipocytes.

Example 5

Identification of Effects of PC on Expression of AMPK/ACC and MAPK/Akt Signaling Pathways The MAPK/Akt and AMPK/ACC signaling pathways are involved in the general steps of adipose tissue generation. First, investigation was carried out whether activation of AMPK and ACC by PC plays an important role in inhibiting adipocyte differentiation through Western blotting and real-time PCR. As a result, according to FIG. 4A, the total AMPK and ACC expression levels were unchanged, and PC treatment significantly increased phosphorylation of AMPK and ACC compared to fully differentiated adipocytes.

Next, MAPK and Akt signaling in adipocytes in the presence of PC were investigated by Western Blotting. As a result, according to FIG. 4B, MDI-induced adipocytes expressed high levels of activated ERK, JNK, p38, MAPK kinase, and Akt, but the expression levels of activated MAPK kinase and Akt were significantly reduced dose-dependently by PC. Thus, these results showed that the PC inhibits the general steps of adipocyte differentiation via the AMPK/ACC and MAPK/Akt signaling pathways.

Example 6

Identification of Cytotoxicity of Polygalin C and NEFA in HepG2 Cells

In order to identify cytotoxicity of PC and NEFA in HepG2 cells, various concentrations of PC (0, 5, 10, 25, 50, and 100 μM) or NEFA (0, 0.5, 1, and 2 mM) were treated for 24 hours, and then MTT assay was used to determine cell viability. As a result, according to FIG. 5A, PC showed a non-toxic effect at a concentration of up to 100 μM, and according to FIG. 5B, NEFA showed significant cytotoxicity at a concentration from 1 mM.

To determine the preventive and therapeutic effects of PC in fatty liver-induced cell models, treatment of 1 mM NEFA as well as various concentrations of PC (0, 5, 10, 25, 50 μM) were performed for 24 hours, and then MTT assay was used to determine cell viability. As a result, according to FIG. 5C, significant cytotoxicity was observed when 1 mM NEFA was treated, and cell viability was restored when 50 UM PC was treated.

Example 7

Identification of Effects of PC on Fat Accumulation in Fatty Liver-Induced HepG2 Cells To investigate whether PC has an inhibitory effect on fat accumulation, cells were treated in the presence and absence of PC at various concentrations (0, 25, and 50 μM), using Oil red O staining. As a result, according to FIGS. 5D and 5E, PC dose-dependently inhibited production of lipid droplets compared to liver cells solely treated with NEFA. Thus, PC reduced accumulation of lipid in fatty liver-induced HepG2 cells.

Example 8

Identification of Effects of PC on Expression of Adipogenic Factors and Inflammatory Factors in Fatty Liver-Induced HepG2 Cells Due to treatment of free fatty acids such as NEFA, fatty liver is induced by fat accumulation. In order to determine whether PC inhibits adipogenic factors, the degree of expression of adipogenic factor was examined via Western blotting. As a result, according to FIG. 6A, PC significantly reduced expression levels of FAS and ACC1, which are dose-dependently involved in fatty acid synthesis, compared with NEFA-induced fatty liver cells.

It is known that if the symptoms persist in the fatty liver stage, it causes an inflammatory reaction to develop steatohepatitis. In order to determine whether PC inhibits inflammation induced by fat accumulation, the degree of expression of inflammatory factors was examined via Western blotting. As a result, according to FIG. 6B, the expression of COX-2 induced by NEFA treatment was reduced concentration-dependently upon PC treatment.

These results showed that PC regulates fat accumulation by inhibiting activation of FAS and ACC1 in fatty liver cells caused by NEFA treatment and relieves inflammation induced by fat accumulation.

The foregoing description of the present disclosure is for illustrative purposes only, and a person skilled in the art to which the present disclosure pertains will be able to understand that it may be easily modified into other specific forms without changing the technical idea or essential features of the present disclosure. Therefore, the example embodiments described above should be understood as illustrative in all respects and not restrictive.

The scope of the present disclosure is indicated by the appended claims, and the meaning and scope of the claims and all changes or modified forms derived from the equivalent concept thereof should be construed as being included in the scope of the present disclosure.

---

The invention claimed is:

1. A method of reducing body fat, comprising:
administering a health functional food comprising Polygalin C as an active ingredient to a subject, wherein the Polygalin C inhibits differentiation of preadipocytes into adipocytes, thereby suppressing lipid accumulation; downregulates peroxisome proliferator-activated receptor γ(PPARγ), CCAAT/enhancer-binding protein α (C/EBPα) sterol regulatory element-binding protein 1c (SREBP1c), and fatty acid synthase (FAS), activates AMP-activated protein kinase (AMPK) and acetyl-CoA carboxylase (ACC); and inhibits mitogen-activated protein kinase (MAPK) and protein kinase B (Akt) signaling pathways in the subject.

2. The method of claim 1, wherein the body fat is selected from obesity caused by a high-fat diet or body fat caused by hormonal deficiency due to menopause.

3. The method of claim 1, wherein the Polygalin C is contained in an amount of 0.01 to 50 parts by weight with respect to a total of 100 parts by weight of the health functional food.

4. A method for treating non-alcoholic fatty liver, comprising:
administering a pharmaceutical composition comprising Polygalin C as an active ingredient to a subject, wherein the Polygalin C inhibits differentiation of preadipocytes into adipocytes, thereby suppressing lipid accumulation; downregulates peroxisome proliferator-activated receptor γ (PPARγ), CCAAT/enhancer-binding protein α (C/EBPα), sterol regulatory element-binding protein 1c (SREBP1c), and fatty acid synthase (FAS); activates AMP-activated protein kinase (AMPK) and acetyl-CoA carboxylase (ACC); and inhibits mitogen-activated protein kinase (MAPK) and protein kinase B (Akt) signaling pathways in the subject.

5. The method of claim 4, wherein the non-alcoholic fatty liver is selected from hepatic steatosis or non-alcoholic steatohepatitis.

6. A method of ameliorating non-alcoholic fatty liver, comprising;

administering a health functional food comprising Polygalin C as an active ingredient to a subject, wherein the Polygalin C inhibits differentiation of preadipocytes into adipocytes, thereby suppressing lipid accumulation; downregulates peroxisome proliferator-activated receptor γ (PPARγ), CCAAT/enhancer-binding protein α (C/EBPα), sterol regulatory element-binding protein 1c (SREBP1c), and the fatty acid synthase (FAS); activates AMP-activated protein kinase (AMPK) and acetyl-CoA carboxylase (ACC); and inhibits mitogen activated protein kinase (MAPK) and protein kinase B (Akt) signaling pathways in the subject.

* * * * *

SEQUENCE LISTING

```
<160> NUMBER OF SEQ ID NOS: 14

<210> SEQ ID NO 1
<211> LENGTH: 19
<212> TYPE: DNA
<213> ORGANISM: Artificial Sequence
<220> FEATURE:
<223> OTHER INFORMATION: CEBP BETA Forward Primer

<400> SEQUENCE: 1
agcggctgca gaagaaggt                                          19

<210> SEQ ID NO 2
<211> LENGTH: 21
<212> TYPE: DNA
<213> ORGANISM: Artificial Sequence
<220> FEATURE:
<223> OTHER INFORMATION: CEBP BETA Reverse Primer

<400> SEQUENCE: 2
ggcagctgct tgaacaagtt c                                       21

<210> SEQ ID NO 3
<211> LENGTH: 19
<212> TYPE: DNA
<213> ORGANISM: Artificial Sequence
```

-continued

<220> FEATURE:
<223> OTHER INFORMATION: CEBP DELTA Forward Primer

<400> SEQUENCE: 3
agcggctgca gaagaaggt                                                    19

<210> SEQ ID NO 4
<211> LENGTH: 22
<212> TYPE: DNA
<213> ORGANISM: Artificial Sequence
<220> FEATURE:
<223> OTHER INFORMATION: CEBP DELTA Reverse Primer

<400> SEQUENCE: 4
ctggagggtt tgtttttct gt                                                 22

<210> SEQ ID NO 5
<211> LENGTH: 20
<212> TYPE: DNA
<213> ORGANISM: Artificial Sequence
<220> FEATURE:
<223> OTHER INFORMATION: PPAR GAMMA Forward Primer

<400> SEQUENCE: 5
ggtgaaactc tgggagattc                                                   20

<210> SEQ ID NO 6
<211> LENGTH: 20
<212> TYPE: DNA
<213> ORGANISM: Artificial Sequence
<220> FEATURE:
<223> OTHER INFORMATION: PPAR GAMMA Reverse Primer

<400> SEQUENCE: 6
caaccattgg gtcagctctt                                                   20

<210> SEQ ID NO 7
<211> LENGTH: 20
<212> TYPE: DNA
<213> ORGANISM: Artificial Sequence
<220> FEATURE:
<223> OTHER INFORMATION: CEBP ALPHA Forward Primer

<400> SEQUENCE: 7
aggtgctgga gttgaccagt                                                   20

<210> SEQ ID NO 8
<211> LENGTH: 20
<212> TYPE: DNA
<213> ORGANISM: Artificial Sequence
<220> FEATURE:
<223> OTHER INFORMATION: CEBP ALPHA Reverse Primer

<400> SEQUENCE: 8
cagcctagag atccagcgac                                                   20

<210> SEQ ID NO 9
<211> LENGTH: 20
<212> TYPE: DNA
<213> ORGANISM: Artificial Sequence
<220> FEATURE:
<223> OTHER INFORMATION: FAS Forward Primer

<400> SEQUENCE: 9
ttgctggcac tacagaatgc                                                   20

-continued

```
<210> SEQ ID NO 10
<211> LENGTH: 21
<212> TYPE: DNA
<213> ORGANISM: Artificial Sequence
<220> FEATURE:
<223> OTHER INFORMATION: FAS Reverse Primer

<400> SEQUENCE: 10
aacagcctcc agagcgacaa t                                                 21

<210> SEQ ID NO 11
<211> LENGTH: 20
<212> TYPE: DNA
<213> ORGANISM: Artificial Sequence
<220> FEATURE:
<223> OTHER INFORMATION: SREBP1c Forward Primer

<400> SEQUENCE: 11
atcgcaaaca agctgacctg                                                   20

<210> SEQ ID NO 12
<211> LENGTH: 20
<212> TYPE: DNA
<213> ORGANISM: Artificial Sequence
<220> FEATURE:
<223> OTHER INFORMATION: SREBP1c Reverse Primer

<400> SEQUENCE: 12
agatccaggt ttgaggtggg                                                   20

<210> SEQ ID NO 13
<211> LENGTH: 19
<212> TYPE: DNA
<213> ORGANISM: Artificial Sequence
<220> FEATURE:
<223> OTHER INFORMATION: GAPDH Forward Primer

<400> SEQUENCE: 13
gccacatcgc tcagacacc                                                    19

<210> SEQ ID NO 14
<211> LENGTH: 20
<212> TYPE: DNA
<213> ORGANISM: Artificial Sequence
<220> FEATURE:
<223> OTHER INFORMATION: GAPDH Reverse Primer

<400> SEQUENCE: 14
cccaatacga ccaaatccgt                                                   20
```